United States Patent
Shikata et al.

(10) Patent No.: US 10,335,830 B2
(45) Date of Patent: Jul. 2, 2019

(54) ULTRASONIC PROBE

(71) Applicant: Toshiba Medical Systems Corporation, Otawara-shi (JP)

(72) Inventors: Hiroyuki Shikata, Nasushiobara (JP); Takeshi Miyagi, Fujisawa (JP); Kengo Okada, Kawasaki (JP); Fumiyasu Sakaguchi, Otawara (JP); Satoru Tezuka, Nasushiobara (JP); Takashi Takeuchi, Otawara (JP); Yasuhiro Ona, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 500 days.

(21) Appl. No.: 15/131,419

(22) Filed: Apr. 18, 2016

(65) Prior Publication Data

US 2016/0375466 A1    Dec. 29, 2016

(30) Foreign Application Priority Data

Jun. 26, 2015 (JP) .................... 2015-128979
Jan. 25, 2016 (JP) .................... 2016-011759

(51) Int. Cl.
| | |
|---|---|
| *B06B 1/06* | (2006.01) |
| *G01N 29/02* | (2006.01) |
| *G01N 29/24* | (2006.01) |
| *G01N 29/32* | (2006.01) |

(52) U.S. Cl.
CPC ......... *B06B 1/0622* (2013.01); *G01N 29/245* (2013.01); *G01N 29/32* (2013.01); *G01N 2291/0289* (2013.01); *G01N 2291/044* (2013.01); *G01N 2291/106* (2013.01)

(58) Field of Classification Search
CPC ..... B06B 1/0622; G01N 29/245; G01N 29/32
USPC .......... 310/317, 322, 326, 327, 334
See application file for complete search history.

(56) References Cited

U.S. PATENT DOCUMENTS

| | | | | |
|---|---|---|---|---|
| 4,841,977 A | * | 6/1989 | Griffith ............ | A61B 8/12 |
| | | | | 29/25.35 |
| 9,867,596 B2 | * | 1/2018 | Kobayashi ......... | A61B 8/546 |
| 2011/0248603 A1 | * | 10/2011 | Tezuka ............... | A61B 8/4405 |
| | | | | 310/314 |
| 2014/0058269 A1 | * | 2/2014 | Irie .................. | A61B 8/4444 |
| | | | | 600/462 |

(Continued)

FOREIGN PATENT DOCUMENTS

| | | |
|---|---|---|
| JP | 1-262848 | 10/1989 |
| JP | 5-123317 | 5/1993 |

(Continued)

*Primary Examiner* — Thomas M Dougherty
(74) *Attorney, Agent, or Firm* — Oblon, McClelland, Maier & Neustadt, L.L.P.

(57) ABSTRACT

According to one embodiment, an ultrasonic probe includes piezoelectric elements, a flexible printed circuit, and one of an air gap layer and a resin layer. The piezoelectric elements transmit and receive ultrasonic waves. The flexible printed circuit located on a rear surface side of the piezoelectric elements and electrically connected to the piezoelectric elements. The air gap layer locates on a rear surface side of the flexible printed circuit and has air gaps. The resin layer is obtained by filling the air gap layer with a resin and locates on the rear surface side of the flexible printed circuit.

20 Claims, 10 Drawing Sheets

(56) References Cited

U.S. PATENT DOCUMENTS

2015/0245815 A1* 9/2015 Wakabayashi ....... A61B 8/4494
367/140

FOREIGN PATENT DOCUMENTS

| JP | 7-222743 | 8/1995 | |
|---|---|---|---|
| JP | 2013-150681 A * | 8/2013 | ............... A61B 8/00 |

* cited by examiner

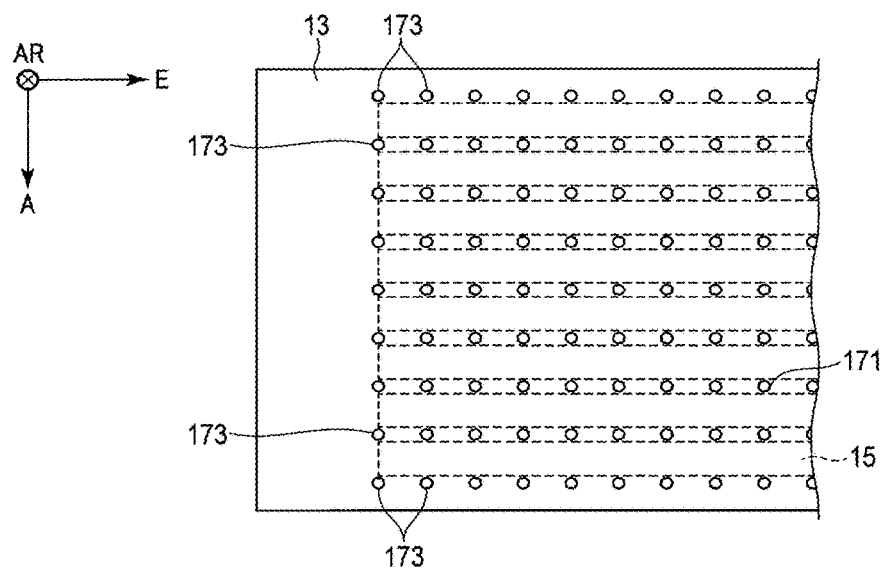
F I G. 3
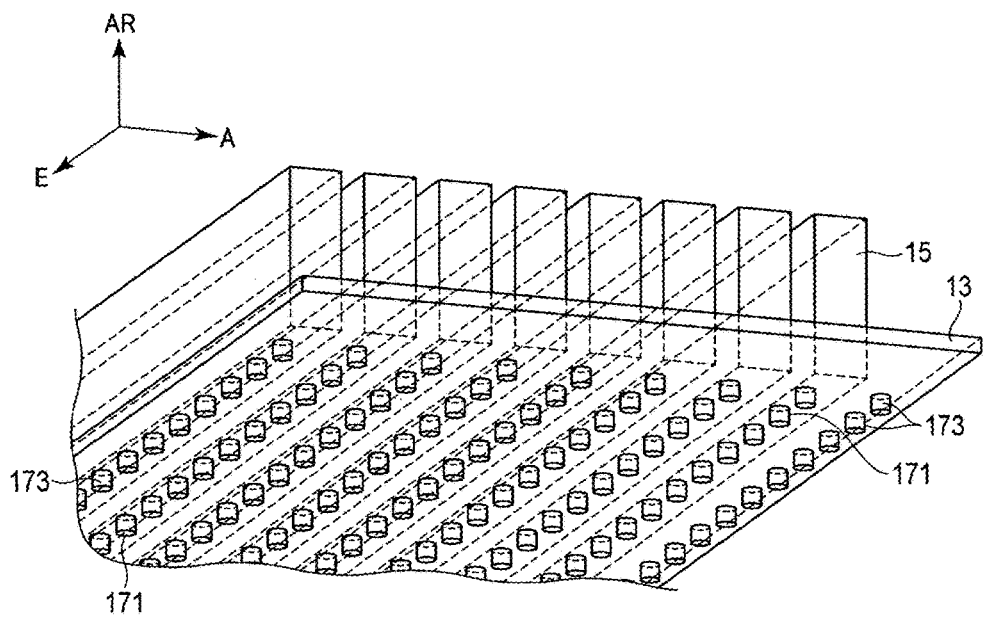
F I G. 4

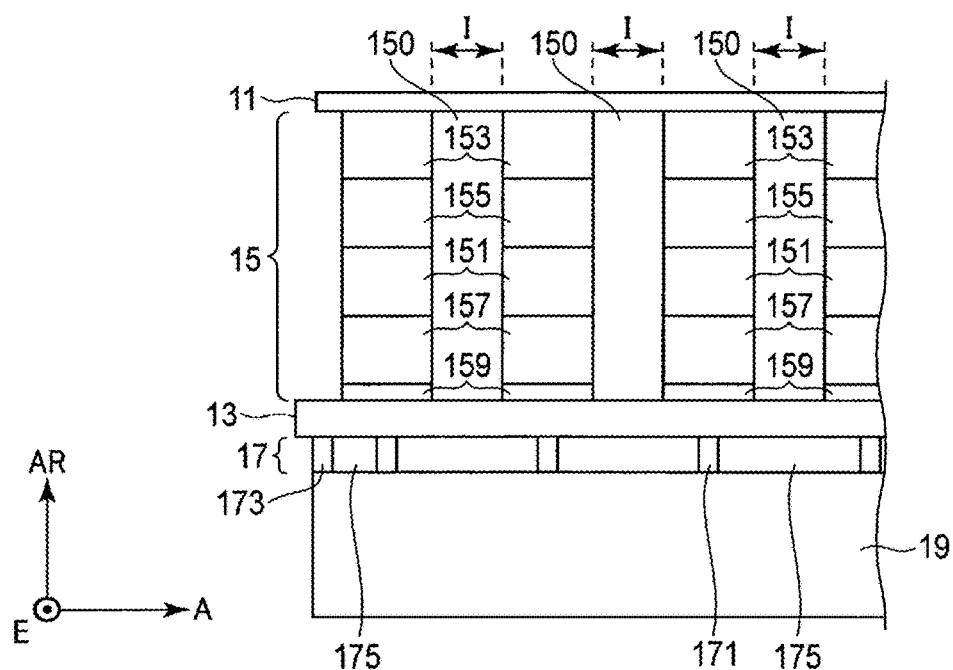
F I G. 5

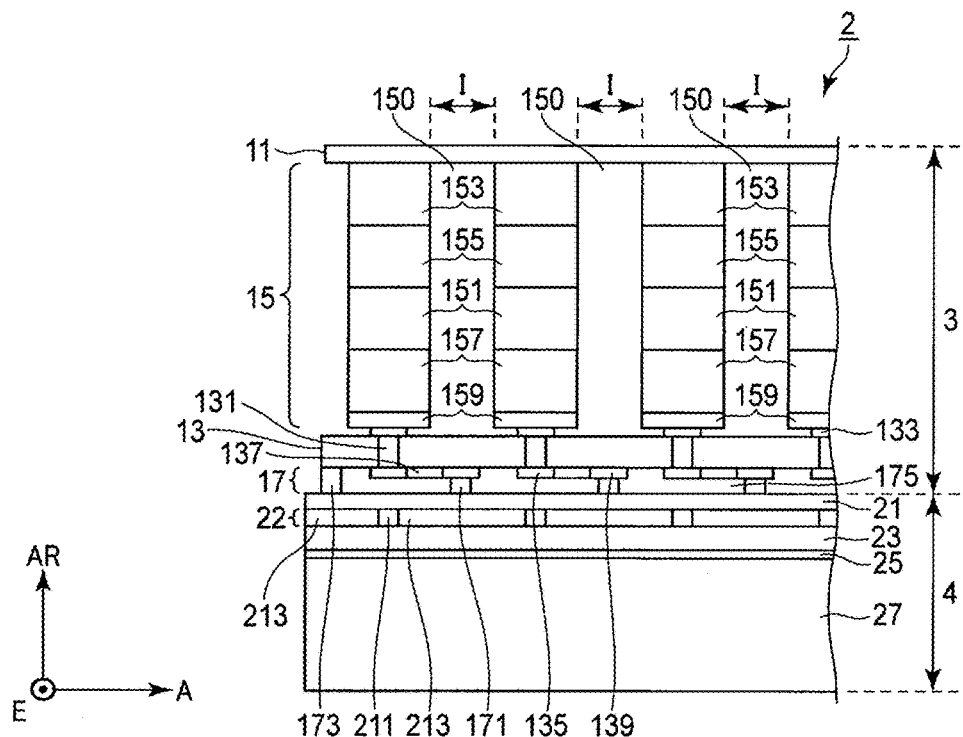
F I G. 6
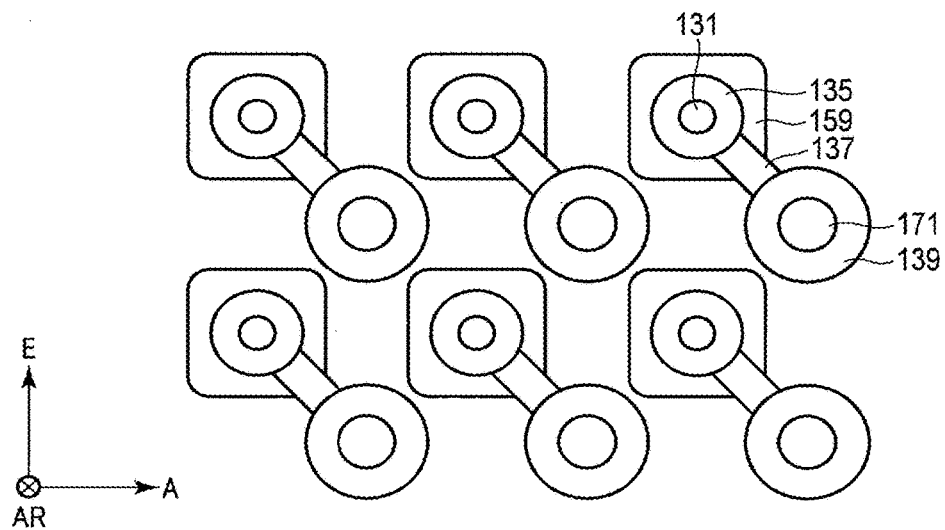
F I G. 7

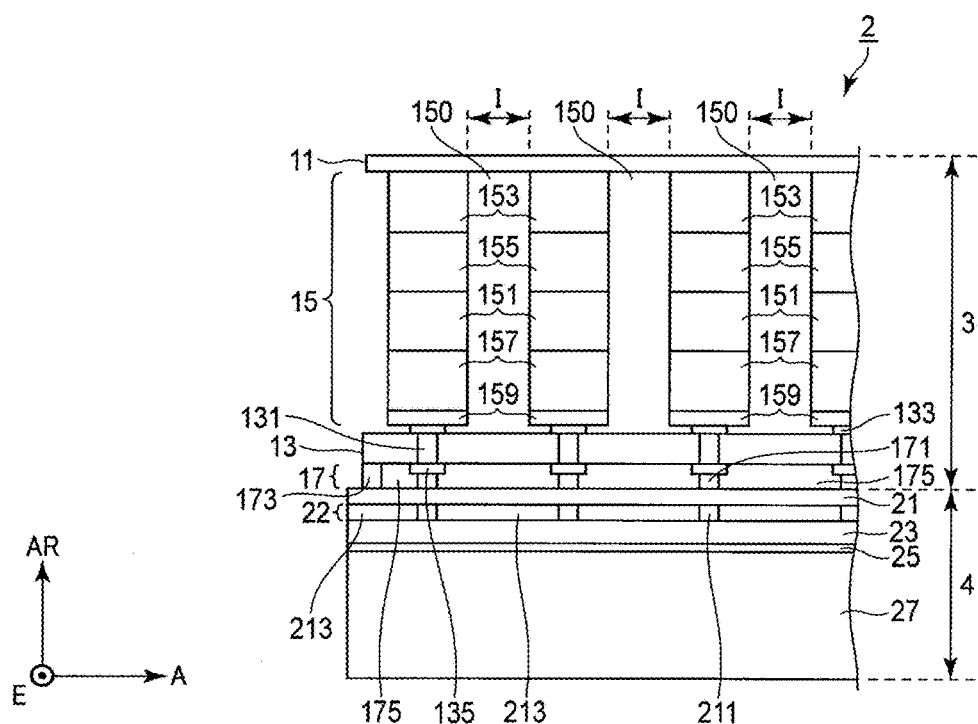
F I G. 12

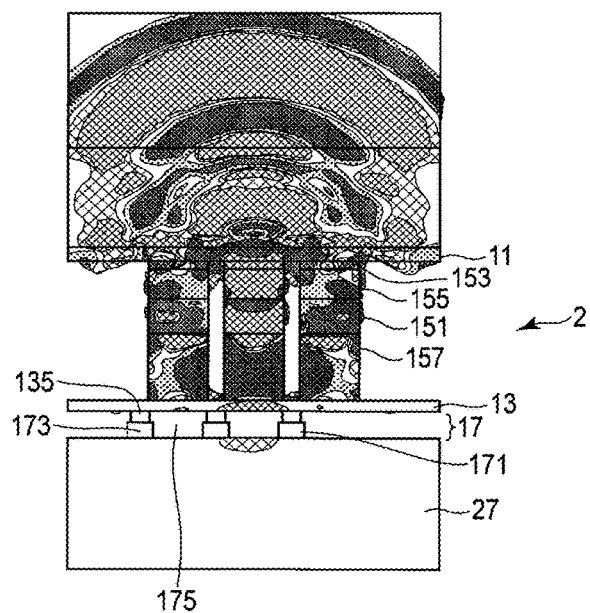
F I G. 14
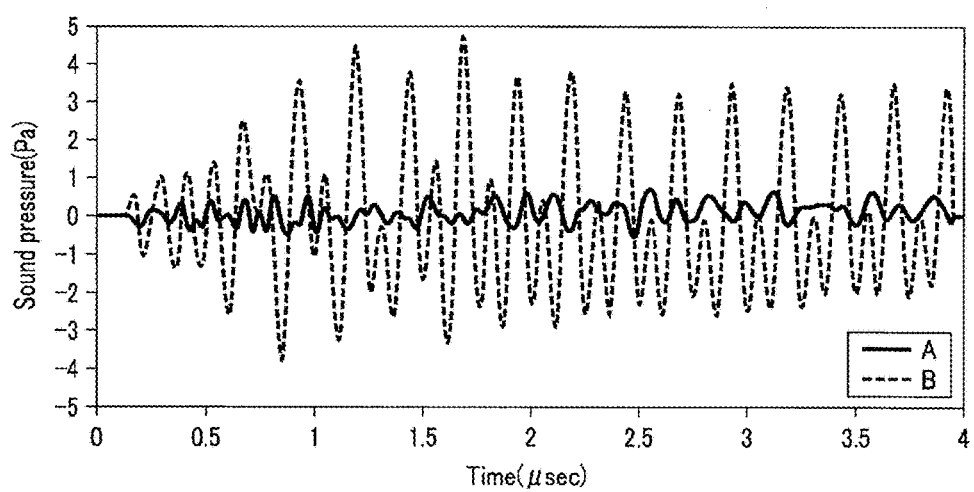
F I G. 15

ULTRASONIC PROBE

CROSS-REFERENCE TO RELATED APPLICATIONS

This application is based upon and claims the benefit of priority from the prior Japanese Patent Application No. 2015-128979, filed Jun. 26, 2015 and the prior Japanese Patent Application No. 2016-011759, filed Jan. 25, 2016, the entire contents of all of which are incorporated herein by reference.

FIELD

Embodiments described herein relate generally to an ultrasonic probe used in an ultrasonic diagnostic apparatus or the like.

BACKGROUND

A two-dimensional array probe, as an ultrasonic probe, which has a plurality of transducers arranged in a matrix pattern uses an enormous number of transducers, and hence it is difficult to directly connect all the transducers to a diagnostic apparatus. For this reason, an IC (Integrated Circuit: integrated circuit chip, ASIC (Application Specific Integrated Circuit) dedicated to a transmission/reception circuit, or the like) for performing ultrasonic transmission/reception and delay addition is sometimes directly mounted on the rear surface side of each transducer.

In addition, a structure such as a substrate called an IP (Interposer) for the mounting of an IC is sometimes added to the rear surface side of each of a plurality of transducers. As a substrate (IP) for the implementation of an ASIC and connection with a transducer, a ceramic substrate made of alumina or the like is used. The use of IPs provides merits in terms of the addition of interconnections, the relocation of pads, and the like as compared with the direct mounting of ASICs on the rear surfaces of transducers.

An IP or IC is independently connected to each transducer with a solder bump, gold bump, or the like formed on the lower surface of the transducer. When using a solder bump, a plate-like transducer is tentatively mounted on an IP or IC first, and the solder is then melted by reflow. Subsequently, the melted solder is cooled to fix the transducer and the IP or the transducer and the IC to each other. When using a gold bump, a plate-like transducer coated with a conductive adhesive agent is tentatively mounted on an IP or IC first, and the resultant structure is heated in a hardening furnace to fix the transducer and the IP or the transducer and the IC to each other.

When fixing a transducer and an IP and a transducer and an IC to each other, in order to prevent the fracture of the IC due to, for example, an external force, the mounting surface of the IC, i.e., the air gap between the transducer and the IP and the air gap between the transducer and the IC, is filled with an adhesive agent called an underfill (to be referred to as a UF hereinafter) which is a liquid hardening resin in consideration of reliability. After the underfill is hardened, a cut groove is formed, extending from the upper surface of the plate-like transducer to midway in the underfill. This leads to the execution of a step of separating each transducer.

When cutting a transducer on an ASIC, there is a risk that a cut process will cause mechanical damage to the ASIC. In addition, it becomes difficult to inspect the acoustic quality of the transducer.

An IC is made of a silicon single crystal. An IP is, for example, a ceramic substrate made of an alumina ceramic material. That is, both an IC and an IP are made of materials having very high hardness. Each of these materials has a high acoustic impedance and a very low acoustic attenuation rate. For this reason, any structure cannot block acoustic propagation to the ASIC or IP. For the above reasons, when ultrasonic waves are emitted to the rear surface side of each transducer, sound waves easily propagate to the rear surface structures of the IC and IP to cause sound reverberation. This will generate a false image on an ultrasonic image.

For example, the following two methods are available as methods of reducing acoustic energy on the rear surface side of each ultrasonic transducer:

(1) providing the rear surface of a transducer with an air gap; and (2) making a material having a very high acoustic impedance (e.g., tungsten or its carbide) tightly adhere to the rear surface of a piezoelectric transducer.

According to method (1) described above, the lower surface of each transducer is a free end, which vibrates with a ½ wavelength. According to method (2), the lower surface of each transducer is a fixed end, which vibrates with a ¼ wavelength. In either of the methods, the very large acoustic impedance difference from the rear surface side of the transducer reduces acoustic radiation to the rear surface side of the transducer. This increases the ratio of radiation onto the front surface side of the transducer, leading to an improvement in transmission sensitivity.

In the structure in method (2), since the thickness of each piezoelectric element is about half the usual thickness (½ wavelength), the electrostatic capacitance of the element increases, and the electric impedance decreases. This further improves the transmission sensitivity.

In a transducer having an air gap as in method (1) described above, however, since the acoustic impedance of air can be almost neglected as compared with a piezoelectric element, the transducer has very high performance in blocking radiation to the rear surface. However, as described above, it is very difficult to implement such a structure with the transducers of a two-dimensional array probe.

For example, there is available a method of ensuring air gaps on transducer surfaces by filling separation grooves between transducers with an adhesive agent and forming protruding shapes from the lower surfaces of the transducers. This, however, requires cumbersome steps after an element cutting step, such as adhesive agent filling, base material removal, and electrode formation. At the same time, the adhesive agent filled between the elements increases the crosstalk between the adjacent elements.

There is also available a structure in which a trench structure is formed in an effective portion of the rear surface of each transducer to support the transducer at only the two ends. However, with such a structure, it is easily imagined that when a pressure from the front surface of each transducer is applied, the element becomes susceptible to breakage, and the reliability deteriorates. In addition, a two-dimensional array probe cannot adopt this structure because each transducer has no ineffective portion.

In addition, in the case of a transducer having a rear surface layer with a high acoustic impedance that described in method (2), since the acoustic impedance ratio between the air gap structure and the flat layer of the transducer is low, acoustic radiation to the rear surface side occurs at a predetermined ratio. Furthermore, in a two-dimensional array probe, when a bump structure like that described above is used for transducer connection, since bumps themselves are a metal, the bumps become acoustic paths between the transducers and the substrates (IPs) or ICs. At the same time, acoustic waves also propagate along the underfill to cause acoustic radiation to the rear surface side of each transducer.

In the case of a two-dimensional array transducer having a structure like that described in method (2), it is necessary to greatly thin the structure on the rear surface side of the transducer. An IP needs to have a predetermined thickness because of its functional limitation, i.e., necessity to use a multilayer interconnection. For this reason, it is necessary to directly connect an IC to the transducer via a bump without using any IP. The roles of an IP are to, for example, adjust the pad position of an IC relative to a transducer, enhance the power supply performance, and serve as a control interconnection as well as facilitating IC mounting. Each IP needs to implement these roles within a corresponding IC. Although each IC can be processed to have a thickness of 100 μm or less by a polishing process, there is a risk of damaging the IC by handling (processing) at the time of IC mounting.

In addition, since a two-dimensional array transducer having a structure like that described in method (2) is based on the assumption that acoustic radiation to the rear surface side of each transducer occurs, a rear surface load member which absorbs unnecessary acoustic energy is required on the rear surface of each IC. In addition, a rear surface load member is required to have a high acoustic impedance acoustically matching with a silicon single crystal and high sound wave absorbing performance, and hence it is necessary to use a very special material. This leads to an increase in manufacturing cost. Furthermore, since it is necessary to execute an array cutting step while each transducer is mounted on a corresponding IC, there is a risk of mechanically or chemically damaging each IC.

In addition, a rubber-based material which absorbs ultrasonic waves is used for a rear-surface member of each transducer of an ultrasonic probe to attenuate ultrasonic waves. However, a rubber-based material has characteristics such as low hardness and a low glass transition point, and is morphologically unstable. That is, a rubber-based material is deformable and hence is not suitable for the basis of a structure. In addition, a rubber-based material generally has a low thermal conductivity and hence requires a process such as being kneaded with a special material, e.g., carbon fibers, to disperse heat generated from a transducer. Furthermore, when using a rubber-based material for a rear-surface member, it is necessary to add a metal or a powder such as a compound powder to the rubber-based material to bring an acoustic impedance close to a design value. For this reason, the use of a rubber-based material for a rear-surface member will lead to an increase in cost.

BRIEF DESCRIPTION OF THE DRAWING

FIG. 3 is a view showing an example of an air gap layer on a cross-section perpendicular to the azimuth direction and the elevation direction in the ultrasonic probe according to the first embodiment;

FIG. 4 is a perspective view showing an air gap layer supported on a support member, a plurality of connecting members in the air gap layer, a flexible printed circuit, and a plurality of transducers in the ultrasonic probe according to the first embodiment;

FIG. 5 is a view showing an example of providing the connecting members immediately below the transducers via the flexible printed circuit in the ultrasonic probe according to the first embodiment;

FIG. 6 is a view showing an example of a cross-section perpendicular to the elevation direction in an ultrasonic probe according to the second embodiment;

FIG. 7 is a cross-sectional view showing an air gap layer on a cross-section perpendicular to the azimuth direction and the elevation direction when viewed from the front surface of a relay substrate in the direction of the rear surface of a flexible printed circuit in the ultrasonic probe according to the second embodiment;

FIG. 12 is a view showing an example of providing the connecting members immediately below the transducers via the flexible printed circuit in the ultrasonic probe according to the second embodiment;

FIG. 14 is a view showing an example of a sound pressure distribution in the same phase as that in FIG. 13 when connecting members are arranged immediately below dividing grooves in the ultrasonic probe according to the second embodiment;

FIG. 15 is a graph showing temporal changes in sound pressure at the same position on a heat dissipation member in the ultrasonic probe associated with the embodiment in FIG. 13 and the ultrasonic probe associated with this embodiment in FIG. 14 according to the second embodiment.

DETAILED DESCRIPTION

Figure 1:
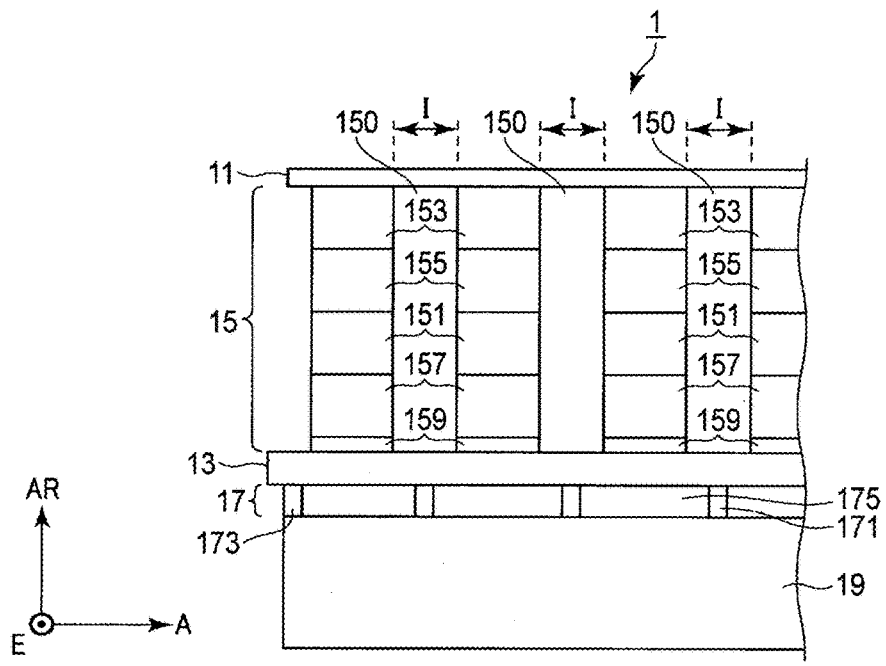
FIG. 1 is a view showing an example of a cross-section perpendicular to the elevation direction in an ultrasonic probe according to the first embodiment.

In general, according to one embodiment, an ultrasonic probe includes piezoelectric elements, a flexible printed circuit, and one of an air gap layer and a resin layer. The piezoelectric elements transmit and receive ultrasonic waves. The flexible printed circuit located on a rear surface side of the piezoelectric elements and electrically connected to the piezoelectric elements. The air gap layer locates on a rear surface side of the flexible printed circuit and has air gaps. The resin layer is obtained by filling the air gap layer with a resin and locates on the rear surface side of the flexible printed circuit.

First Embodiment

An ultrasonic probe according to the first embodiment will be described below with reference to the accompanying drawing. Note that the same reference numerals in the following description denote constituent elements having almost the same arrangements, and a repetitive description will be made only when required.

FIG. 1 is a view showing an example of a cross-section perpendicular to the elevation direction in an ultrasonic probe 1 according to the first embodiment. The ultrasonic probe 1 according to this embodiment is a one-dimensional array probe. The one-dimensional array probe 1 includes a plurality of transducers arrayed in the array direction or azimuth direction.

Figure 2:
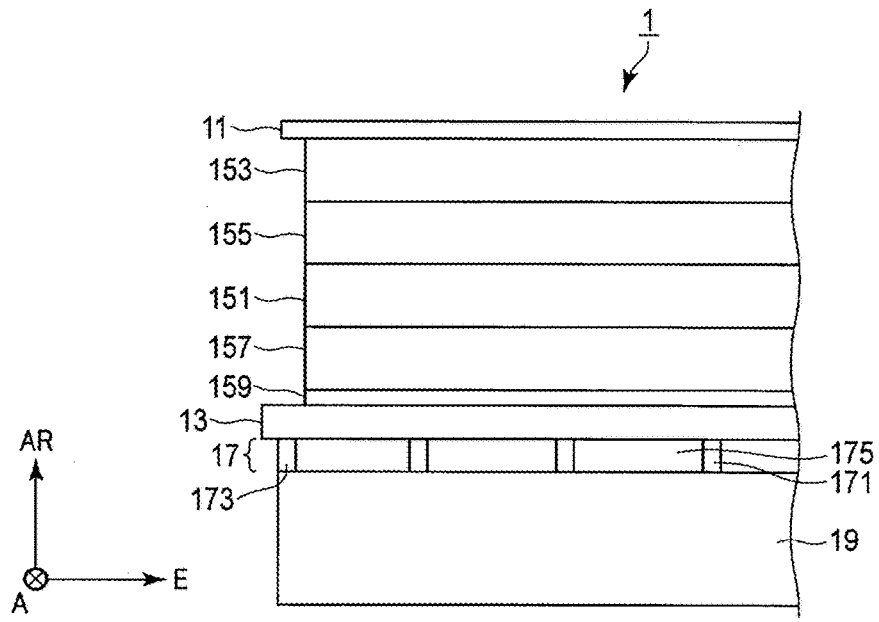
FIG. 2 is a view showing an example of a cross-section perpendicular to the azimuth direction in the ultrasonic probe according to the first embodiment.

Referring to FIG. 1, the elevation direction is a direction (direction E) perpendicular to the drawing surface. The azimuth direction is a direction (direction A) in which the plurality of transducers are arrayed. A direction perpendicular to the azimuth direction and the elevation direction is a direction (direction AR) associated with acoustic radiation. FIG. 2 is a view showing an example of a cross-section perpendicular to the azimuth direction in the ultrasonic probe 1 according to this embodiment.

As shown in FIGS. 1 and 2, the one-dimensional array probe 1 according to this embodiment includes a common electrode 11, a flexible printed circuit (FPC) 13, a plurality of transducers 15, an air gap layer 17, and a support member 19. The plurality of transducers 15 are arrayed on the flexible printed circuit 13 along the azimuth direction so as to be separated from each other by dividing grooves 150 each having a predetermined interval I. That is, the plurality of transducers 15 are provided on the flexible printed circuit 13 in a strip pattern. A predetermined gas (e.g., air) is sealed in each of the plurality of dividing grooves 150 along the elevation direction.

The common electrode 11 is provided on the front surfaces of the plurality of transducers 15. Referring to FIG. 1, the common electrode 11 is jointed to first acoustic matching layers 153 over the plurality of transducers 15. More specifically, the common electrode 11 is physically and electrically joined to the plurality of first acoustic matching layers 153. The common electrode 11 is formed from, for example, a copper foil. An interconnection led from the common electrode 11 is connected, in an arbitrary form, to a cable (not shown) via, for example, an interconnection on the flexible printed circuit 13. An acoustic lens (not shown) is joined to the front surface of the common electrode 11. In addition, a cover (living body contact member) (not shown) which covers the acoustic lens is provided on the front surface of the acoustic lens.

The flexible printed circuit 13 has a non-divided structure, and is joined to the plurality of transducers 15. That is, the flexible printed circuit 13 supports the plurality of transducers 15. The flexible printed circuit 13 may have a plurality of interconnections respectively corresponding to the plurality of transducers 15. In this case, the plurality of transducers 15 are electrically connected to the plurality of interconnections, respectively.

Each of the plurality of transducers 15 includes a piezoelectric element 151, the first acoustic matching layer 153, a second acoustic matching layer 155, a high-impedance layer (rear surface acoustic matching layer) 157, and an individual electrode 159. The plurality of transducers 15 are arrayed on the flexible printed circuit 13 at predetermined intervals I along the azimuth direction.

That is, the plurality of transducers 15 are physically separated from each other by the dividing grooves 150 along the elevation direction, each having the predetermined interval I parallel to the azimuth direction. Each of the plurality of transducers 15 is joined on the flexible printed circuit 13 which is not cut, and hence is structurally stable.

The second acoustic matching layer 155 is joined to the front surface of each piezoelectric element 151 in the acoustic radiation direction, and the first acoustic matching layer 153 is joined to the front surface of the second acoustic matching layer 155. The high-impedance layer 157 is joined to the rear surface of the piezoelectric element 151. The individual electrode 159 is joined to the rear surface of the high-impedance layer 157. The first acoustic matching layer 153, the second acoustic matching layer 155, and the high-impedance layer 157 each have conductivity.

Each piezoelectric element 151 is a piezoelectric transducer which is shaped into a rectangular shape having long sides along the elevation direction and short sides along the azimuth direction and is associated with transmission/reception of ultrasonic waves. A piezoelectric transducer is, for example, a piezoelectric ceramic element. The piezoelectric element 151 generates ultrasonic waves upon receiving a driving signal (electrical signal) supplied from an ultrasonic diagnostic apparatus or ultrasonic flaw detection apparatus (not shown) via an electronic circuit (not shown). The piezoelectric element 151 generates an echo signal (electrical signal) upon receiving ultrasonic waves reflected by an object or a substance associated with ultrasonic flaw detection. The generated echo signal is supplied to the ultrasonic diagnostic apparatus or ultrasonic flaw detection apparatus via a cable (not shown) connected to the ultrasonic probe.

The first acoustic matching layer 153 and the second acoustic matching layer 155 are provided on the ultrasonic irradiation side (front surface side) of each piezoelectric element 151. The first acoustic matching layer 153 and the second acoustic matching layer 155 each are formed from an acoustic matching material such as epoxy resin containing a metal powder made of a conductive material. It is possible to achieve acoustic impedance matching between an object and the piezoelectric element 151 by adjusting physical parameters such as acoustic velocities, thicknesses, and acoustic impedances of the first acoustic matching layer 153 and the second acoustic matching layer 155.

More specifically, the first acoustic matching layer 153 and the second acoustic matching layer 155 suppress the reflection of ultrasonic waves caused by the difference between the acoustic impedance of an object or a substance associated with ultrasonic flaw detection and the acoustic impedance of each piezoelectric element 151. Note that although FIG. 1 shows the two-layer acoustic matching layer (the first acoustic matching layer 153 and the second acoustic matching layer 155), this embodiment is not limited to this. For example, an acoustic matching layer including one layer, three layers, or four or more layers may be arranged on the front surface of the piezoelectric element 151 and jointed to it.

The high-impedance layer 157 is joined to the rear surface of each of a plurality of piezoelectric elements. That is, the high-impedance layer 157 is located between each of the plurality of piezoelectric elements 151 and the flexible printed circuit 13. The high-impedance layer 157 has an acoustic impedance higher than that of the piezoelectric element 151. The high-impedance layer 157 is formed from tungsten or a carbide of tungsten. Note that the high-impedance layer 157 may be omitted from the arrangement of each transducer 15.

The individual electrode 159 is joined to the rear surface of each high-impedance layer 157. The individual electrode 159 is formed by, for example, metal plating or sputtering using silver, gold, or the like.

FIG. 3 is a view showing an example of the air gap layer 17 on a cross-section vertical to the direction AR perpendicular to the elevation direction and the azimuth direction in the ultrasonic probe 1 according to this embodiment. FIG. 4 is a perspective view showing the air gap layer 17 supported on the support member 19, a plurality of connecting members 171 and 173 in the air gap layer 17, the flexible printed circuit 13, and the plurality of transducers 15 in the ultrasonic probe 1 according to the embodiment.

The air gap layer 17 is provided on the rear surface side of the flexible printed circuit 13. For example, the air gap layer 17 is provided between the flexible printed circuit 13 and the support member 19. The air gap layer 17 includes the plurality of connecting members 171 and 173 and air gap portions 175. As shown in FIGS. 1 and 2, each of the plurality of connecting members 171 and 173 connects a front-surface structure on the front surface of the air gap layer 17 and a rear-surface structure on the rear surface of the air gap layer 17.

As shown in FIGS. 1, 2, 3, and 4, the front-surface structures include, for example, the common electrode 11, the flexible printed circuit 13, the plurality of transducers 15 in a strip pattern, and the acoustic lens (not shown). The rear-surface structures include, for example, the support member 19, as shown in FIGS. 1 and 2.

As shown FIGS. 1, 2, 3, and 4, each connecting member 171 has a columnar structure. Many connecting members 171 and 173 are arranged on the front surface side of the support member 19 in correspondence with the transducers 15. As shown FIGS. 1, 2, 3, and 4, the plurality of connecting members 171 are provided, immediately below (right behind) the dividing grooves 150 which divide the transducers 15, on the rear surface side of the flexible printed circuit 13.

That is, the connecting members 171 and 173 are located at positions between the two nearest piezoelectric elements 151 on the rear surface side of the flexible printed circuit 13. As shown FIGS. 1, 2, 3, and 4, the plurality of connecting members 173 located on end portions of the air gap layer 17 are arranged outside the transducers 15 in the azimuth direction and the elevation direction. With this structure, the air gap portions 175 are hermetically sealed. Note that, as shown in FIG. 5, the connecting members 171 may be provided immediately below (right behind) the transducers 15 through the flexible printed circuit 13.

More specifically, one end (tip) of each of the connecting members 171 and 173 is bonded to the flexible printed circuit 13 immediately below the corresponding dividing groove 150 with an adhesive agent or the like. The other end (tip) of each of the connecting members 171 and 173 is bonded to the support member 19 immediately below the corresponding dividing groove 150 with an adhesive agent or the like. When bonding the connecting members 171 and 173 to the flexible printed circuit 13 and bonding the connecting members 171 and 173 to the support member 19, the air gap portions 175 are filled with no adhesive agent or the like.

That is, the air gap portions 175 are regions in which a gas (e.g., air) having an acoustic impedance lower than that of front-surface structures is sealed. With the structure described above, the ultrasonic probe 1 can be kept in a structurally stable state.

When interconnections associated with transducers are pulled out of the flexible printed circuit 13, the connecting members 171 and 173 need not be conductors. In this case, the connecting members 171 and 173 each may be a solder resist (e.g., a thermosetting epoxy resin film) or the like applied on the flexible printed circuit 13. In addition, the connecting members 171 and 173 may be conductors. In this case, the connecting members 171 and 173 each are a copper bump obtained by forming a copper plating into a thick columnar shape.

The support member 19 is formed from a high-hardness metal (e.g., aluminum) because of no acoustic reflection to the rear surface side. That is, the support member 19 of the ultrasonic probe 1 according to this embodiment is a support having mechanical stability and supporting the front-surface structures described above.

According to the arrangement described above, the following effects can be obtained.

The one-dimensional array probe (ultrasonic probe) 1 according to this embodiment includes the flexible printed circuit 13, on the rear surface side of the transducer 15, which is not cut nor separated, and the air gap layer 17 provided on the rear surface side of the flexible printed circuit 13. The air gap portions 175 in the air gap layer 17 can suppress acoustic radiation to the rear surface side of the transducer 15 as much as possible in the ultrasonic probe 1 according to the embodiment. This can improve sensitivity toward the front surface side. In addition, the one-dimensional array probe 1 according to the embodiment further includes the high-impedance layers 157 on the rear surfaces of the piezoelectric elements 151. This can further reduce acoustic radiation to the rear surface side of each transducer 15 and hence further improve sensitivity toward the front surface side.

In addition, the one-dimensional array probe 1 according to this embodiment allows one-dimensional array transducers 15 to be formed on the undivided flexible printed circuit 13. This simplifies a manufacturing process and hence can achieve a reduction in manufacturing cost. In addition, this facilitates inspecting the acoustic quality of each transducer. Furthermore, since a gas can be sealed in the dividing grooves 150, crosstalk between adjacent transducers is reduced.

In addition, the one-dimensional array probe 1 according to this embodiment has the plurality of connecting members 171 provided on the rear surface side of the flexible printed circuit 13 at positions immediately below the dividing grooves 150, which divide the transducers 15. This provides each transducer 15 with an air gap structure between itself and the flexible printed circuit 13, and hence can further reduce acoustic radiation in the rear surface direction. That is, this embodiment can efficiently block backward radiation from each transducer 15. Therefore, the one-dimensional array probe 1 according to the embodiment efficiently emits power injected at the time of transmission as ultrasonic waves to the front surface side.

Furthermore, the one-dimensional array probe 1 according to this embodiment allows rear-surface structures to be formed from a high-hardness material (e.g., a metal), and hence requires no acoustic absorbing material, leading to a reduction in manufacturing cost.

As described above, the one dimensional array probe 1 according to this embodiment allows the formation of a one dimensional array while ensuring an air gap structure on the rear surface of each transducer 15. An air gap structure can efficiently suppress backward radiation from each transducer 15, and hence improve acoustic separation performance. In addition, the ultrasonic probe 1 according to the embodiment has the mechanically stable structure using the flexible printed circuit 13, and hence can achieve a reduction in manufacturing cost and efficiently implement energy conversion. In addition, the ultrasonic probe can reduce the influence of acoustic radiation in the rear surface direction on ultrasonic images.

(Modification)

An ultrasonic probe according to this modification differs from the ultrasonic probe 1 according to the first embodiment in that it has a resin layer with a predetermined underfill being filled or arranged in the air gap portions 175, in place of the air gap layer 17. Note that the same reference numerals as those in the first embodiment denote constituent elements having almost the same arrangements in the following description, and a repetitive description will be made only when required.

Figure 16:
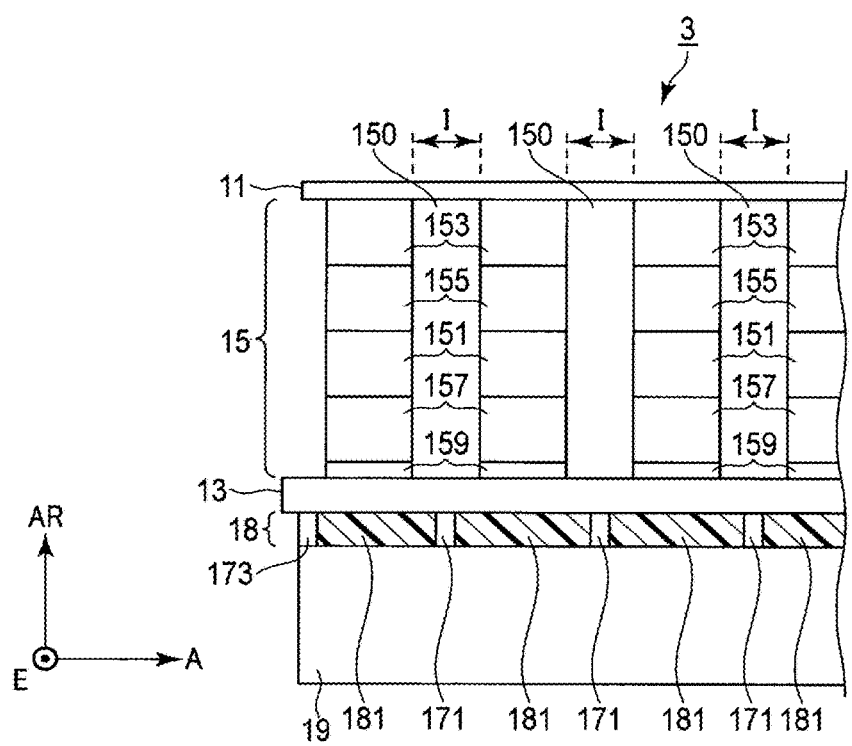
FIG. 16 is a view showing an example of a cross-section perpendicular to the elevation direction in the ultrasonic probe according to a modification of the first embodiment.

FIG. 16 is a view showing an example of a cross-section perpendicular to the elevation direction in an ultrasonic probe 3 according to this modification. As shown in FIG. 16, a resin layer 18 has a structure having an underfill filled or arranged in the air gap portions 175 of the air gap layer 17 according to the first embodiment.

The resin layer 18 is provided on the rear surface side of the flexible printed circuit 13. For example, the resin layer 18 is provided between the flexible printed circuit 13 and the support member 19. The resin layer 18 includes the plurality of connecting members 171 and 173 and a plurality of resin portions 181. As shown in FIG. 16, the plurality of connecting members 171 and 173 and the plurality of resin portions 181 connect the front-surface structures on the front surface of the resin layer 18 to the rear-surface structures on the rear surface of the resin layer 18.

As shown in FIG. 16, the front-surface structures include, for example, the common electrode 11, the flexible printed circuit 13, the plurality of transducers 15 in a strip pattern, and the acoustic lens (not shown). The rear-surface structures include, for example, the support member 19, as shown in FIG. 16.

As shown in FIG. 16, each connecting member 171 has a columnar structure. The many connecting members 171 and 173 are arranged on the front surface side of the support member 19 with respect to the transducers 15. As shown in FIG. 16, the plurality of connecting members 171 are arranged at positions different from positions right behind the piezoelectric elements 151. In other words, the plurality of connecting members 171 are provided on the rear surface side of the flexible printed circuit 13 at positions immediately below (right behind) the dividing grooves 150, which divide the transducers 15.

That is, the connecting members 171 and 173 each are located on the rear surface side of the flexible printed circuit 13 at a position between the two nearest piezoelectric elements 151. As shown in FIG. 16, the plurality of connecting members 173 located on end portions of the air gap layer 17 are arranged outside the transducers 15 in the azimuth direction and the elevation direction.

The space between each pair of adjacent connecting members of the plurality of connecting members corresponds to the resin portion 181 in which an underfill is arranged. The underfill has an acoustic impedance lower than that of the front-surface structures. In this case, the underfill is a resin such as epoxy resin or silicone (an organic silicon compound polymer).

More specifically, one end (tip) of each of the connecting members 171 and 173 is joined to the flexible printed circuit 13 at a position immediately below the dividing groove 150 with an adhesive agent or the like. In addition, the resin portions 181 in the resin layer 18 bond the front surface structures to the rear surface structures. When bonding the connecting members 171 and 173 to the flexible printed circuit 13 and bonding the connecting members 171 and 173 to the support member 19, the resin portion 181 between each pair of adjacent connecting members 171 is filled with the underfill. Note that the resin layer 18 may be integrally formed by the connecting members 173 and the underfill. In this case, the underfill is arranged in the resin portions 181. With the above structure, the ultrasonic probe 3 can be held in a structurally stable state.

According to the arrangement described above, the following effects can be obtained.

The one-dimensional array probe (ultrasonic probe) 3 according to this modification includes, on the rear surface side of the transducers 15, the flexible printed circuit 13, which is neither cut nor separated, and the resin layer 18 provided on the rear surface side of the flexible printed circuit 13. The resin layer 18 includes the plurality of connecting members which connect the front-surface structures on the front surface of the resin layer 18 to the rear-surface structures and the predetermined resin (resin portions 181) arranged in the spaces between the adjacent connecting members of the plurality of connecting members. The connecting members 171 and 173 are arranged at positions different from positions right behind the piezoelectric elements 151, i.e., positions right behind the transducers 15.

With the resin portions 176 in the resin layer 18, the ultrasonic probe 3 according to this modification can suppress acoustic radiation to the rear surface side of each transducer 15 as much as possible. This can improve sensitivity toward the front surface side. When the underfill filled or arranged in the resin portions 181 is silicone, since the density of silicone is lower than that of epoxy resin and the acoustic impedance of silicone is lower than that of epoxy resin, the effect of suppressing acoustic radiation to the rear surface side of each transducer 15 is larger than that obtained when the underfill filled or arranged in the resin portions 181 is epoxy resin.

In addition, the resin portions 176 in the resin layer 18 can suppress the tailing vibrations of the vibrations of the transducers 15 over a long period of time. When, for example, the underfill filled or arranged in the resin portions 181 is epoxy resin, the effect of suppressing tailing vibrations is larger than when the underfill filled or arranged in the resin portions 181 is silicone.

As described above, a resin to be filled in the resin portions 181 in the resin layer 18 can be properly selected in accordance with the application or the like of the ultrasonic probe 3, and is not limited to epoxy resin or silicone.

In addition, the one-dimensional array probe 3 according to this modification includes the high-impedance layers 157 on the rear surfaces of the piezoelectric elements 151. This can further reduce acoustic radiation to the rear surface side of each transducer 15, and improve sensitivity toward the front surface side.

In addition, the one-dimensional array probe 3 according to this modification can form the one-dimensional transducers 15 on the undivided flexible printed circuit 13. This simplifies a manufacturing process and hence can achieve a reduction in manufacturing cost. In addition, this facilitates inspecting the acoustic quality of each transducer. Furthermore, since a gas can be sealed in the dividing grooves 150, crosstalk between adjacent transducers is reduced.

In addition, the one-dimensional array probe 3 according to this modification has the plurality of connecting members 171 provided on the rear surface side of the flexible printed circuit 13 at positions immediately below the dividing grooves 150, which divide the transducers 15. This provides each transducer 15 with a resin structure between itself and the flexible printed circuit 13, and hence can further reduce acoustic radiation in the rear surface direction. That is, this modification can efficiently block backward radiation from each transducer 15. Therefore, the one-dimensional array probe 3 according to the modification efficiently emits power injected at the time of transmission as ultrasonic waves to the front surface side.

As described above, the one-dimensional array probe 3 according to this modification allows the formation of a one-dimensional array while ensuring a resin structure on the rear surface of each transducer 15. This can improve acoustic separation performance. In addition, the ultrasonic probe 3 according to the modification has the mechanically stable structure by using the resin layer 18. This improves the reliability of the ultrasonic probe 3 in terms of rigidity, and hence can achieve a reduction in manufacturing cost and efficiently implement energy conversion. In addition, the ultrasonic probe can reduce the influence of acoustic radiation in the rear surface direction on ultrasonic images.

Second Embodiment

An ultrasonic probe according to the second embodiment will be described below with reference to the accompanying drawing. Note that the same reference numerals as in the first embodiment denote constituent elements having almost the same arrangements in the following description, and a repetitive description will be made only when required. This embodiment includes, on the lower surface of each transducer, a flexible printed circuit which is neither cut nor separated and an air gap layer on the rear surface side of the flexible printed circuit. Columnar structures exist between the flexible printed circuit and structures on the rear surface side at positions immediately below (right behind) the transducers and support array transducers. A two-dimensional array, in particular, includes columnar structures at the intersections of dividing grooves of transducers in a matrix pattern. This can efficiently suppress acoustic radiation to the rear surface side of each array transducer.

FIG. 6 is a view showing an example of a cross-section perpendicular to the elevation direction in an ultrasonic probe 2 according to the second embodiment. The ultrasonic probe 2 according to this embodiment is a two-dimensional array probe. The two-dimensional array probe 2 includes a plurality of transducers arrayed along the azimuth direction (first direction) and the elevation direction (second direction) perpendicular to the azimuth direction.

Referring to FIG. 6, the elevation direction is a direction (direction E) perpendicular to the drawing surface, the azimuth direction is a direction (direction A) perpendicular to the elevation direction, and a direction perpendicular to the azimuth direction and the elevation direction is a direction (direction AR) associated with acoustic radiation. A cross-section perpendicular to the azimuth direction in the ultrasonic probe 2 as a two-dimensional array probe is the same as that shown in FIG. 6.

As shown in FIG. 6, the two-dimensional array probe 2 according to this embodiment includes a common electrode 11, a flexible printed circuit 13, a plurality of transducers 15, an air gap layer 17, a relay substrate 21, ICs (Integrated Circuits) 23, and a heat dissipation member 27.

The common electrode 11 is provided on the front surfaces of the plurality of transducers 15. A cover (living body contact member) (not shown) is provided on the front surface of the common electrode 11. That is, the ultrasonic probe 2 according to this embodiment is a two-dimensional array probe, and hence requires no acoustic lens.

Each of the plurality of transducers 15 includes a piezoelectric element 151, a first acoustic matching layer 153, a second acoustic matching layer 155, a high-impedance layer (rear surface acoustic matching layer) 157, an individual electrode 159, and an independent pad (not shown). The plurality of transducers 15 are arrayed on the flexible printed circuit 13 at predetermined intervals I along the azimuth direction and the elevation direction.

More specifically, the plurality of transducers 15 are separated by the dividing grooves 150 having predetermined intervals I and arrayed in a matrix pattern on the flexible printed circuit 13 along the azimuth direction and the elevation direction. The dividing grooves 150 have the predetermined intervals I parallel to the azimuth direction and the predetermined intervals I parallel to the elevation direction. The plurality of transducers 15 are physically separated from each other by the dividing grooves 150 arrayed along the azimuth direction and the elevation direction.

Note that the predetermined interval I in the azimuth direction may differ in length from the predetermined interval I in the elevation direction. Each of the plurality of transducers 15 is joined on the undivided flexible printed circuit 13, and hence is structurally stable. A predetermined gas (e.g., air) is sealed in each of the plurality of dividing grooves 150 arranged along the elevation direction and the azimuth direction.

Each piezoelectric element 151 is a piezoelectric transducer which is shaped to have almost the same width in the elevation direction and the azimuth direction. The piezoelectric element 151 generates ultrasonic waves upon receiving a driving signal (electrical signal) supplied via the integrated circuit 23. The piezoelectric element 151 generates an echo signal (electrical signal) upon receiving ultrasonic waves reflected by an object or a substance associated with ultrasonic flaw detection. The generated echo signal is supplied to the integrated circuit 23.

Independent pads (not shown) are electrically and physically connected to the individual electrodes 159 on the lower surfaces of the transducers 15. That is, each independent pad is provided immediately below the individual electrode 159 of a corresponding one of the transducers 15. Each independent pad is, for example, a copper foil for soldering. The independent pad has conductivity and electrically and physically joined to a land 133 provided in a through hole 131 in the flexible printed circuit 13.

The flexible printed circuit 13 has an undivided structure and is joined to the plurality of transducers 15. That is, the flexible printed circuit 13 supports the plurality of transducers 15. The flexible printed circuit 13 is a two-sided plate having copper foil interconnection patterns on the obverse and reverse surfaces. The flexible printed circuit 13 has, immediately below each transducer 15, the through hole 131 which connects the two surfaces of the flexible printed circuit 13.

Each through hole 131 is a through hole extending through the flexible printed circuit 13 in the AR direction. The number of through holes 131 corresponds to the number of transducers 15 in the two-dimensional array probe 2.

The through holes 131 include two types: a through hole whose wall surface is plated; and a non-through hole plated upon removal of a base layer from the rear surface of the flexible printed circuit 13, with a conductor on one surface of the flexible printed circuit 13 being left unremoved. This embodiment may use either of the two types of holes. In addition, the inner surface of each through hole 131 may be filled with a conductive material. Note that an end portion of each through hole 131 in the reverse surface (rear surface) of the flexible printed circuit 13 may be subjected to an insulating process with a solder resist or the like so as to be covered by it.

The land (to be referred to as the front-surface land hereinafter) 133 is provided on an end portion of each through hole 131 in the front surface of the flexible printed circuit 13. Each front-surface land 133 is joined to an independent pad provided immediately below the individual electrode 159 of a corresponding one of the transducers 15. A land (to be referred to as rear-surface land hereinafter) 135 is provided on an end portion of each through hole 131 in the rear surface of the flexible printed circuit 13. Each rear-surface land 135 is electrically connected to a corresponding one of interconnection patterns 137 on the rear surface of the flexible printed circuit 13.

The interconnection patterns 137 on the rear surface of the flexible printed circuit 13 are interconnection patterns for electrically connecting the rear-surface lands 135 to bump connecting pads (to be referred to as connecting pads hereinafter) 139. Each connecting pad 139 is provided on the rear surface of the flexible printed circuit 13 at a position immediately below (on the rear surface side) the interval between the two second nearest piezoelectric elements 151 (or transducers 15).

That is, each interconnection pattern 137 is a conductor provided on the rear surface of the flexible printed circuit 13 to electrically connect a position immediately below the transducer 15 to a position immediately below the intersection between the dividing groove 150 extending along the elevation direction and the dividing groove 150 extending along the azimuth direction. In other words, the interconnection patterns 137 are interconnections which electrically one-to-one connect the rear-surface lands 135 to the connecting pads 139 which are respectively nearest to the rear-surface land 135.

The number of connection pads 139 corresponds to the number of through holes 131. That is, the plurality of connecting pads 139 are respectively electrically connected to the plurality of transducers 15. In other words, the rear-surface land 135 connected to the through hole 131 and the connecting pad 139 are independently connected to each of the plurality of transducers 15 via the interconnection pattern 137.

Figure 8:
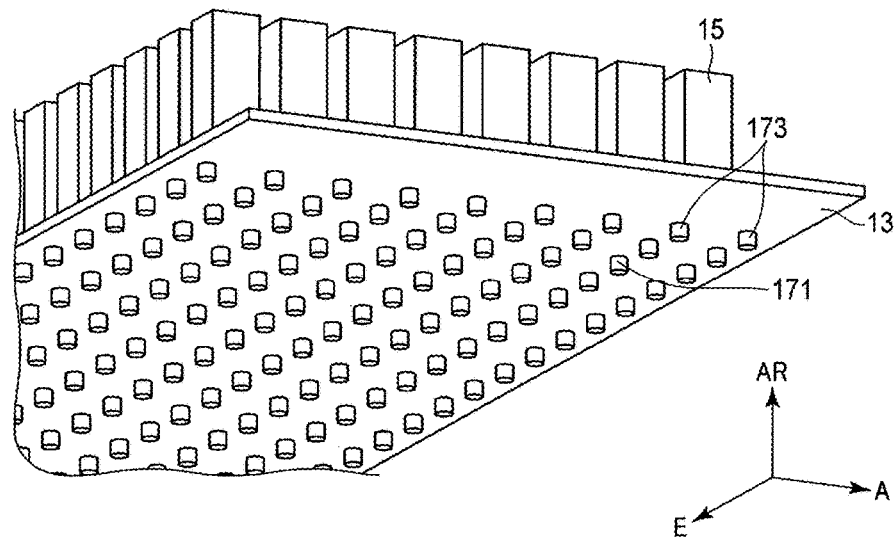
FIG. 8 is a perspective view showing the air gap layer, a plurality of connecting members in the air gap layer, a flexible printed circuit, and a plurality of transducers in the ultrasonic probe according to the second embodiment.

FIG. 7 is a cross-sectional view of the air gap layer 17 on a cross-section perpendicular to the direction AR when viewed from the front surface of the relay substrate 21 in the direction of the rear surface of the flexible printed circuit 13 in the ultrasonic probe 2 according to the second embodiment. FIG. 8 is a perspective view showing the air gap layer 17, a plurality of connecting members 171 and 173 in the air gap layer 17, the flexible printed circuit 13, and the plurality of transducers 15 in the ultrasonic probe 2 according to this embodiment.

The air gap layer 17 is provided on the rear surface side of the flexible printed circuit 13. For example, the air gap layer 17 is provided between the flexible printed circuit 13 and the relay substrate 21. Note that when the relay substrate 21 is omitted, the air gap layer 17 is provided between the flexible printed circuit 13 and the integrated circuits 23.

The air gap layer 17 includes the plurality of connecting members 171 and 173 and air gap portions 175. As shown in FIG. 6, each of the connecting members 171 and 173 connects a front-surface structure on the front surface of the air gap layer 17 to a rear-surface structure on the rear surface of the air gap layer 17. As shown in FIG. 6, front-surface structures include, for example, the common electrode 11, the flexible printed circuit 13, and the plurality of transducers 15 in a matrix pattern. As shown in FIG. 6, rear-surface structures include, for example, the relay substrate 21, the integrated circuits 23, and the heat dissipation member 27.

Referring to FIG. 7, an illustration of the flexible printed circuit 13 is omitted. As shown in FIG. 7, each individual electrode 159 is joined to the corresponding front surface land 133 via an independent pad (not shown). Referring to FIG. 7, each front surface land 133 overlaps the corresponding rear surface land 135, and hence is not shown here.

Each through hole 131 is located in the central portions of the corresponding front-surface land 133 and the corresponding rear-surface land 135. Each rear-surface land 135 is joined to one end of the corresponding interconnection pattern 137 arranged on the rear surface of the flexible printed circuit 13. The other end of the interconnection pattern 137 is connected to the connecting pad 139. The connecting member 171 is joined to central portion of the connecting pad 139.

As shown in FIGS. 6, 7, and 8, the connecting members 171 and 173 have columnar structures. The connecting members 171 and 173 function as electric contacts to the relay substrate 21 and the integrated circuits 23 as rear-surface structures. For this reason, the connecting members 171 and 173 always have conductivity. The connecting members 171 and 173 having conductive columnar structures are copper bumps formed on conductors (connecting pads 139) on the rear surface side of the flexible printed circuit 13 or gold bumps or solder bumps on the relay substrate 21 or the integrated circuits 23.

When using copper bumps or gold bumps, the connecting members 171 and 173 having conductivity and columnar structures are connected and fixed to the relay substrate 21 by a technique using a conductive paste or the like. When using solder bumps, the connecting members are connected and fixed to the relay substrate 21 by a method using reflow or the like. Note that when the relay substrate 21 is omitted, the connecting members 171 and 173 are connected and fixed to the integrated circuits 23. When bonding the connecting pads 139 on the flexible printed circuit 13 to the connecting members 171 and 173 and bonding the connecting members 171 and 173 to the relay substrate 21, the air gap portions 175 are not filled with an adhesive agent.

The many connecting members 171 and 173 are arranged on the front surface side of the relay substrate 21 in correspondence with the connecting pads 139 with respect to the transducers 15. As shown in FIGS. 6, 7, and 8, the plurality of connecting members 171 and 173 are provided on the rear surface side of the flexible printed circuit 13 at, for example, positions immediately below (right behind) the intersection points between the dividing grooves 150 along the elevation direction and the dividing grooves 150 in the azimuth direction.

That is, the connecting members 171 and 173 each are located on the rear surface side of the flexible printed circuit 13 at a position immediately below (right behind) the interval between the two second nearest piezoelectric elements 151 or immediately below (right behind) the interval between the two nearest piezoelectric elements 151. That is, the connecting member 173 is arranged on the rear surface side at the position of the intersection point between two diagonal lines of a rectangle (e.g., a square) defined by the positions of four dielectric elements surrounding the rectangle. As shown in FIGS. 6 and 8, the plurality of connecting members 173 located on end portions of the air gap layer 17 are arranged outside the transducers 15 in the azimuth direction and the elevation direction. With this structure, the air gap portions 175 are sealed and hermitically closed.

Figure 9:
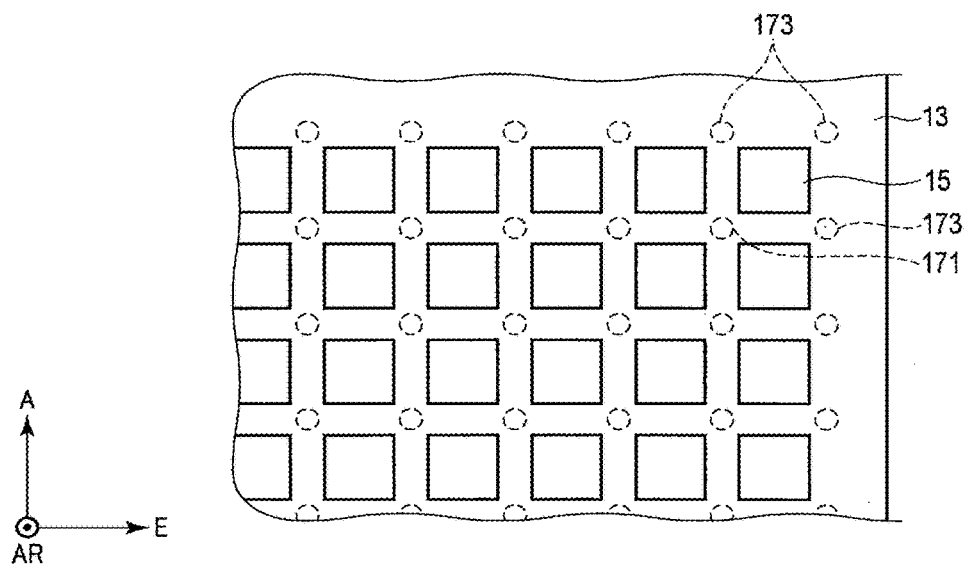
FIG. 9 is a view when a plurality of transducers in a matrix pattern provided on a flexible printed circuit are viewed from a direction perpendicular to the azimuth direction and the elevation direction in the ultrasonic probe according to the second embodiment.

FIG. 9 is a view when a plurality of transducers 15 in a matrix pattern provided on the flexible printed circuit 13 are viewed from the direction AR. As shown in FIG. 9, the connecting members 171 and 173 are provided immediately below the intersection points between the dividing grooves 150 along the elevation direction and the dividing grooves 150 along the azimuth direction. As shown in FIG. 9, the plurality of connecting members 173 located on end portions of the air gap layer 17 are arranged outside the transducers 15 in the azimuth direction and the elevation direction.

Note that each connecting pad 139 is provided on the rear surface of the flexible printed circuit 13 at a position immediately below (right behind) the interval between the two nearest piezoelectric elements 151 (or transducers 15). That is, each connecting pad 139 may be provided on the rear surface of the flexible printed circuit 13 at a position immediately below at least one of the dividing groove 150 along the elevation direction and the dividing groove 150 along the azimuth direction. At this time, each of the connecting members 171 and 173 is provided on the rear surface of the flexible printed circuit 13 at a position immediately below the interval between the two nearest piezoelectric elements 151.

Figure 10:
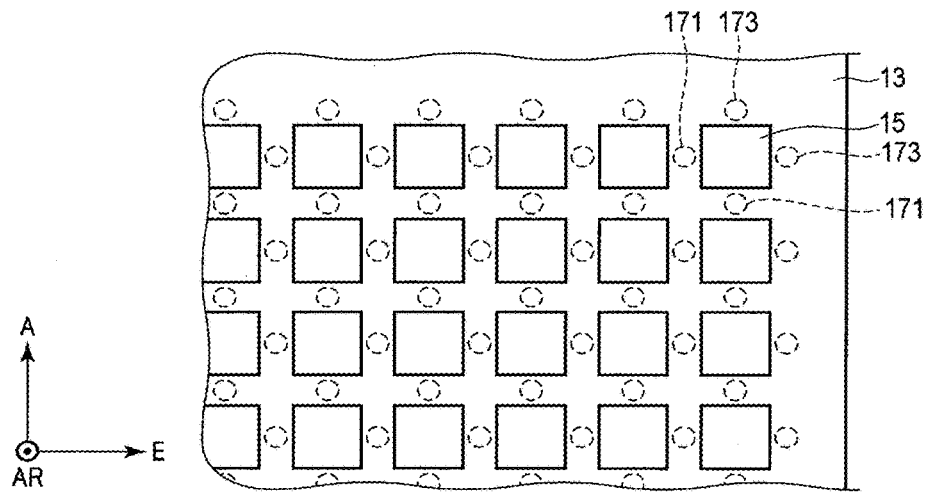
FIG. 10 is a view when the plurality of transducers in the matrix pattern provided on the flexible printed circuit are viewed from the direction perpendicular to the azimuth direction and the elevation direction in the ultrasonic probe according to the second embodiment.

FIG. 10 is a view when the plurality of transducers 15 in the matrix pattern provided on the flexible printed circuit 13 are viewed from the direction AR. As shown in FIG. 10, the connecting members 171 and 173 are provided immediately below the dividing grooves 150 along the elevation direction and immediately below the dividing grooves 150 in the azimuth direction. In addition, the plurality of connecting members 173 located on end portions of the air gap layer 17 are arranged outside the transducers 15 in the azimuth direction and the elevation direction, as shown in FIG. 10.

As shown in FIGS. 6, 7, 8, 9, and 10, the two-dimensional array probe 2 according to this embodiment ensures its structural stability by the presence of the undivided flexible printed circuit 13 and the connecting members (columnar structures) 171 and 173 arranged at almost the same density as that of the transducers 15.

Figure 11:
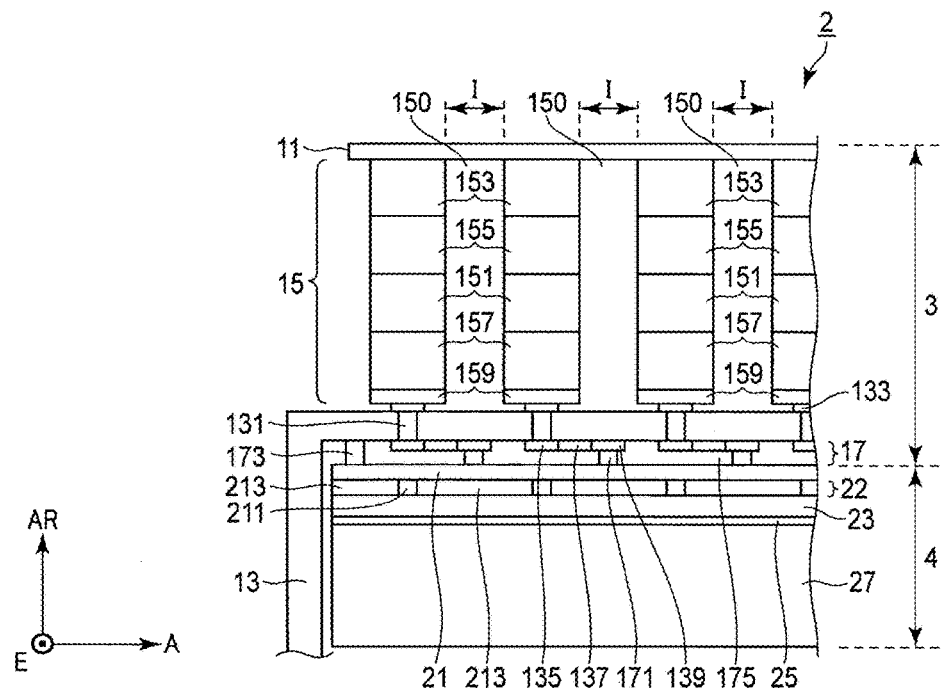
FIG. 11 is a view showing how the flexible printed circuit supporting the plurality of transducers extends along a heat dissipation member to extract signals from a relay substrate in the ultrasonic probe according to the second embodiment.

Note that the flexible printed circuit 13 supporting the plurality of transducers 15 may be elongated along the heat dissipation member 27 as shown in FIG. 11 to extract signals from the relay substrate 21. Note that, as shown in FIG. 12, the connecting members 171 and 173 may be provided immediately below the transducers 15 via the flexible printed circuit 13.

The relay substrate 21 is provided between the air gap layer 17 and the integrated circuits 23. The relay substrate 21 is a substrate which relays the electrical connection between the flexible printed circuit 13 and the integrated circuits 23. The relay substrate 21 is, for example, an IP (InterPoser). The interposer 21 is a substrate which electrically relays the pitch between two adjacent connecting members of the plurality of connecting members 171 and 173 and the pitch between I/O (Input/Output) terminals on the integrated circuits 23. The interposer 21 is an alumina ceramic substrate having a predetermined thickness.

The front surface of the interposer 21 is provided with electrode pads respectively corresponding to the plurality of transducers 15. More specifically, the electrode pads (not shown) are provided on the front surface of the interposer 21 at positions to face the connecting pads 139. Gold bumps (connecting members 171 and 173) are placed on the electrode pads by a wire bonder machine or the like. When placing gold bumps, the surfaces of the electrode pads (connecting pads 139) on the flexible printed circuit 13 side are coated with a conductive adhesive agent.

The interposer 21 and the flexible printed circuit 13 are aligned with each other. After this alignment, the flexible printed circuit 13 is tentatively (temporarily) mounted on the interposer 21. The adhesive agent between the tentatively mounted interposer 21 and the flexible printed circuit 13 is hardened by a hardening furnace. This establishes electrical continuity between the connecting members 171 and 173 and the interposer 21 and, at the same time, mechanically fixes them to each other.

Solder ball bumps (connecting members 171 and 173) may be formed, in place of gold bumps, on the electrode pads on the interposer 21. In this case, as in the above case, the solder is melted and cooled after tentative mounting by a means such as reflow to establish electrical continuity between the connecting members 171 and 173 and the interposer 21 and fix them to each other. Note that signal extraction from the interposer 21 may be performed by wire bonding, ACF (Anisotropic Conductive Film) bonding, or the like.

The integrated circuits 23 are electronic circuits connected to the interposer 21 by flip-chip bonding or the like. In this case, the space between each integrated circuit 23 and the interposer 21 is filled with an adhesive agent called an underfill 213 which is a liquid curable resin.

Note that each integrated circuit 23 may include a circuit such as an ASIC (Application Specific Integrated Circuit) or a programmable logic device (e.g., an SPLD (Simple Programmable Logic Device), a CPLD (Complex Programmable Logic Device), or an FPGA (Field Programmable Gate Array)).

More specifically, each integrated circuit 23 is joined to the interposer 21 with a bump 211 or ACF provided with respect to the I/O (Input/Output) terminal of the corresponding transducer 15 on the interposer 21. For example, the integrated circuit 23 is mounted on the interposer 21 for each transducer 15. Each of the plurality of integrated circuits 23 respectively corresponding to the plurality of transducers 15 applies a driving signal (driving voltage) to the corresponding transducer 15 electrically connected via the interposer 21, the connecting members 171 and 173, the through hole 131, and the like, under the control of the ultrasonic diagnostic apparatus. The integrated circuits 23 process echo signals generated by the transducers 15 via the interposer 21, the connecting members 171 and 173, the through holes 131, and the like.

The heat dissipation member 27 is joined to the rear surface of each integrated circuit 23 via heat-transfer grease 25. The heat-transfer grease 25 is also called heat dissipation grease. Heat generated by the integrated circuit 23 is transferred to the heat dissipation member 27 via the heat-transfer grease 25. In addition, the heat dissipation member 27 dissipates the heat transferred via the heat-transfer grease 25. According to this embodiment, since almost no ultrasonic waves are reflected to the rear surface side, a material having high hardness and high heat conductivity, e.g., aluminum, can be used for the heat dissipation member 27. In addition, the heat dissipation member 27 has rigidity that can stably support the front-surface structures, the air gap layer 17, the interposer 21, and the integrated circuits 23. This enables the heat dissipation member 27 to improve the mechanical stability and heat dissipation performance of the ultrasonic probe 2.

According to the above arrangement, the following effects can be obtained.

The two-dimensional array probe (ultrasonic probe) 2 according to this embodiment includes, on the rear surface side of each transducer 15, the flexible printed circuit 13 which is neither cut nor separated and the air gap layer 17 provided on the rear surface side of the flexible printed circuit 13. With this structure, in the ultrasonic probe 2 according to the embodiment, the air gap portions 175 in the air gap layer 17 can suppress acoustic radiation to the rear surface side of the transducers 15 as much as possible. This leads to an improvement in acoustic separation performance and an improvement in sensitivity toward the front surface side.

In addition, the two-dimensional array probe 2 according to this embodiment includes the high-impedance layer 157 on the rear surface of each piezoelectric element. This can further reduce acoustic radiation to the rear surface side of each transducer 15, and hence further improve sensitivity toward the front surface side. Furthermore, since a gas (air) can be sealed in the dividing grooves 150, it is possible to reduce crosstalk between the adjacent transducers of the two-dimensional array probe 2.

Figure 13:
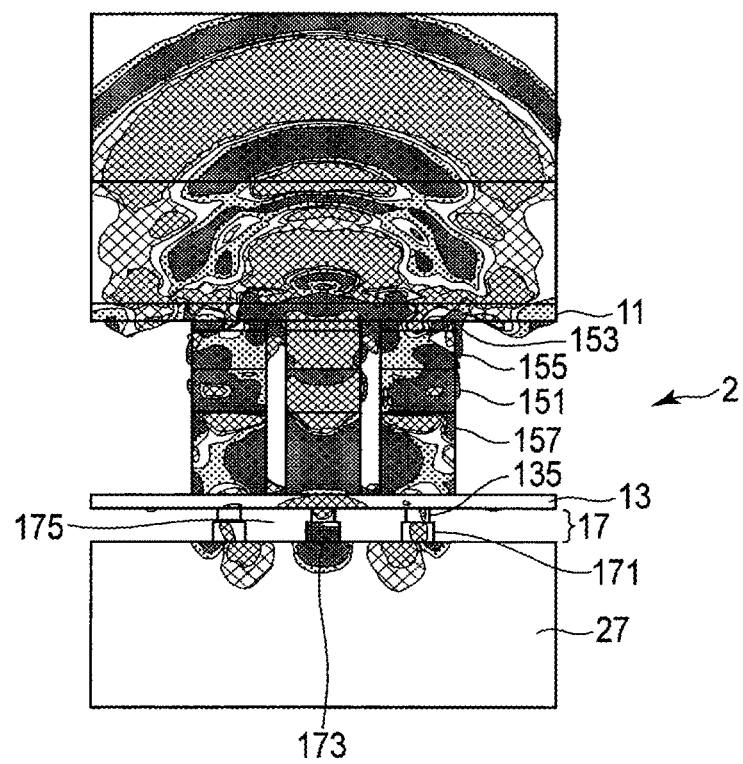
FIG. 13 is a view showing an example of a sound pressure distribution in a given phase when connecting members are arranged immediately below transducers in the ultrasonic probe according to the second embodiment.

FIG. 13 is a view showing an example of a sound pressure distribution in a given phase when the connecting members 171 and 173 are arranged immediately below the transducers 15 according to this embodiment. As shown in FIG. 13, sound pressures propagate to the rear-surface structures only via the connecting members 171 and 173. As is obvious from FIG. 13, the ultrasonic probe 2 according to the embodiment can suppress acoustic radiation to the rear surface side of each transducer 15 as much as possible and reduce crosstalk between the adjacent transducers.

In addition, the two-dimensional array probe 2 according to this embodiment allows two-dimensional array transducers to be formed on the undivided flexible printed circuit 13. That is, the two-dimensional array probe 2 allows independent manufacture of an acoustic portion 3 including the common electrode 11, the flexible printed circuit 13, the transducers 15, and the air gap layer 17 and an electronic circuit portion 4 including the relay substrate (interposer) 21, a connecting layer 22 having bumps and an underfill, the integrated circuits 23, and the heat dissipation member 27.

This makes it possible to easily inspect acoustic quality in the acoustic portion 3 before the electronic circuit portion 4 including the integrated circuits is connected to the acoustic portion 3. As described above, the two-dimensional array probe 2 according to this embodiment can reduce the waste of integrated circuits based on the yield of the acoustic portion 3. In addition, the two-dimensional array probe 2 according to the embodiment can use the interposer 21, and hence improve the design freedom and manufacturing freedom of the electronic circuit portion 4.

In addition, the two-dimensional array probe 2 according to this embodiment allows the plurality of connecting members 171 and 173 to be provided on the rear surface side of the flexible printed circuit 13 at positions immediately below the dividing grooves 150 which divide the transducers 15. This makes each transducer 15 have an air gap structure between itself and the flexible printed circuit 13, and can further reduce acoustic radiation in the rear surface direction. That is, according to the embodiment, it is possible to efficiently block backward radiation from each transducer 15. Therefore, the two-dimensional array probe 2 according to the embodiment emits power injected at the time of transmission as ultrasonic waves to the front surface side.

FIG. 14 is a view showing an example of a sound pressure distribution in the same phase as that in FIG. 13 when the connecting members 171 and 173 are arranged immediately below the dividing grooves 150. As shown in FIG. 14, sound pressures to the rear-surface structures are further reduced as compared with the structure in FIG. 13, and hence rear-surface radiation is efficiently suppressed. As is obvious from FIG. 14, the ultrasonic probe 2 according to the embodiment can further reduce acoustic radiation to the rear surface side of each transducer 15, and reduce crosstalk between the adjacent transducers.

FIG. 15 is a graph showing temporal changes in sound pressure at the same position on the heat dissipation member 27 in the ultrasonic probe according to the embodiment in FIG. 13 and the ultrasonic probe according to the embodiment in FIG. 14. Referring to FIG. 15, a plot A represents a temporal change in sound pressure at a predetermined position on the heat dissipation member 27 in the ultrasonic probe according to the embodiment in FIG. 14. Referring to FIG. 15, a plot B represents a temporal change in sound pressure at a predetermined position on the heat dissipation member 27 in the ultrasonic probe according to the embodiment in FIG. 13. As shown in FIG. 15, the ultrasonic probe according to the embodiment in FIG. 14 efficiently suppresses rear-surface radiation as compared with the ultrasonic probe according to the embodiment in FIG. 13.

In addition, the two-dimensional array probe 2 according to this embodiment allows a rear-surface structure as the heat dissipation member 27 to be made of a high-hardness material (e.g., a metal). This obviates the necessity to use any acoustic absorbing material, and hence can achieve a reduction in manufacturing cost.

As has been described above, the two-dimensional array probe 2 according to this embodiment allows the formation of a two-dimensional array while ensuring air gap structures (air gap portions 175) on the rear surfaces of the transducers 15. The structure according to the embodiment, in particular, allows the flexible printed circuit 13 to be connected to the interposer 21 or the integrated circuits 23 via bumps (connecting members 171 and 173), and hence is suitable for a two-dimensional array. In addition, since the air gap structure is provided on the rear surface of each transducer 15, the acoustic separation performance is high, and acoustic radiation to the rear surface side can be efficiently suppressed.

In addition, according to this embodiment, since an interposer substrate can be used as the relay substrate 21, the design freedom is high in terms of, for example, the relocation of input/output (I/O) pads on the integrated circuits 23. Furthermore, the acoustic portion 3 and the electronic circuit portion 4 can be independently manufactured and inspected first, and the non-defective portions can then be combined to complete a product. This can minimize the influence of yield on cost.

Note that as a modification of this embodiment, like the modification of the first embodiment, an underfill may be filled or arranged in the air gap portions 175. In this case, the two-dimensional array probe 2 according to the embodiment has the structure obtained by replacing the air gap layer 17 by the resin layer 18. In this case, each of the plurality of connecting members on the resin layer 18 is arranged on the rear surface side at a position between two second nearest piezoelectric elements, i.e., on the rear surface side at the position of the intersection position between two diagonal lines of a rectangle (e.g., a square) having corners (edges) at the positions of four piezoelectric elements surrounding the rectangle. Since the structure of the resin layer 18 and effects originating from the resin layer 18 in the first embodiment are the same as those in the modification, a description will be omitted.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic probe comprising:
a plurality of piezoelectric elements configured to transmit and receive ultrasonic waves;
a flexible printed circuit located on a rear surface side of the piezoelectric elements and electrically connected to the piezoelectric elements;
one of an air gap layer located on a rear surface side of the flexible printed circuit and having air gaps, and a resin layer obtained by filling the air gap layer with a resin and located on the rear surface side of the flexible printed circuit;
a plurality of first conductive members electrically connected to the piezoelectric elements, respectively, and disposed on the rear surface of side of the flexible printed circuit, wherein
the plurality of piezoelectric elements are arranged on the printed circuit board with gaps therebetween, and
each of the plurality of first conductive members is disposed at a position corresponding to one of the gaps.

2. The probe according to claim 1, wherein the air gap layer or the resin layer is located on the rear surface of the flexible printed circuit.

3. The probe according to claim 1, further comprising a high-impedance layer located between each of the piezoelectric elements and the flexible printed circuit and having a higher acoustic impedance than those of the piezoelectric elements.

4. The probe according to claim 1, wherein the air gap layer or the resin layer includes a front surface, a rear surface, and a plurality of connecting members configured to connect a front-surface structure on the front surface to a rear-surface structure on the rear surface.

5. An ultrasonic probe, comprising:
a plurality of piezoelectric elements configured to transmit and receive ultrasonic waves;
a flexible printed circuit located on a rear surface side of the piezoelectric elements and electrically connected to the piezoelectric elements;
one of an air gap layer located on a rear surface side of the flexible printed circuit and having air gaps, and a resin layer obtained by filling the air gap layer with a resin and located on the rear surface side of the flexible printed circuit; and
a plurality of connecting members configured to connect a front-surface structure on a front surface of the air gap layer to a rear-surface structure on the rear surface of the air gap layer,
wherein each of the connecting members is located on the rear surface side of the flexible printed circuit at a position between the two nearest piezoelectric elements.

6. The probe according to claim 4, wherein the piezoelectric elements are arrayed along a first direction and a second direction perpendicular to the first direction, and
each of the connecting members is located on the rear surface side of the flexible printed circuit at a position between the two second nearest piezoelectric elements.

7. The probe according to claim 4, wherein each of the connecting members electrically connects the front-surface structure to the rear-surface structure.

8. The probe according to claim 1, further comprising an integrated circuit provided on a rear surface side of the air gap layer or the resin layer and having at least one of functions of driving the piezoelectric elements and processing echo signals generated by vibrations of the piezoelectric elements.

9. The probe according to claim 8, further comprising a relay substrate provided between the integrated circuit and the air gap layer or the resin layer and configured to relay electrical connection between the flexible printed circuit and the integrated circuit.

10. The probe according to claim 1, wherein the piezoelectric elements are arrayed along a first direction, and
the probe further comprises a support member configured to support a rear surface of the air gap layer or the resin layer.

11. The probe according to claim 8, further comprising a heat dissipation member provided on a rear surface of the integrated circuit and configured to dissipate heat generated by the integrated circuit.

12. An ultrasonic probe comprising:
a plurality of piezoelectric elements configured to transmit and receive ultrasonic waves;
a flexible printed circuit located on a rear surface side of the piezoelectric elements and electrically connected to the piezoelectric elements;
a resin layer located on a rear surface side of the flexible printed circuit; and
a rear-surface structure located on a rear surface side of the resin layer,
wherein the resin layer includes a plurality of connecting members configured to connect a front-surface structure on a front surface of the resin layer to the rear-surface structure, and
the connecting members are arranged at a position different from a position right behind the piezoelectric elements.

13. The probe according to claim 12, wherein a predetermined resin is arranged in a space between adjacent connecting members of the connecting members.

14. The probe according to claim 12, wherein each of the connecting members is located on a rear surface side at a position between the two nearest piezoelectric elements.

15. The probe according to claim 12, wherein the piezoelectric elements are arrayed along a first direction and a second direction perpendicular to the first direction, and
each of the plurality of connecting members is located on a rear surface side at a position between the two second nearest piezoelectric elements.

16. The probe according to claim 1, comprising:
second conductive members disposed on a front surface side of the flexible printed circuit and electrically connected to the piezoelectric elements, respectively;

third conductive members disposed on the rear surface side of the flexible printed circuit and each being positioned corresponding to one of the piezoelectric elements;

fourth conductive members each electrically connecting one of the second connecting members to one of the third connecting members; and fifth conductive members each electrically connecting one of the first connecting members to one of third connecting members.

17. The probe according to claim 1, comprising:

one of a substrate and a support member disposed on a side of the air gap layer or resin layer opposite the rear surface layer of the flexible printed circuit, wherein each of the first conductive members is connected to the flexible printed circuit and the one of the substrate and support member.

18. The probe according to claim 1, comprising:

the piezoelectric elements, flexible printed circuit and one of the air gap layer and resin layer being stacked in a stacking direction;

second conductive members each being disposed on the rear surface side of the flexible printed circuit, electrically connected to the piezoelectric elements, and positioned under one of the piezoelectric elements in the stacking direction; and third conductive members each electrically connecting one of the first conductive members to one of second conductive members.

19. The probe according to claim 1, comprising:

the piezoelectric elements formed in a matrix extending in first and second orthogonal directions; and the first conductive members being disposed corresponding to a center of groups of four of the piezoelectric elements disposed in a 2×2 section of the matrix.

20. The probe according to claim 12, comprising:

the connecting members being arranged at a position different from a position directly below the piezoelectric elements.

* * * * *